United States Patent [19]

Norbury et al.

[11] Patent Number: 5,013,473

[45] Date of Patent: May 7, 1991

[54] ENCAPSULATED COSMETIC MATERIALS AND PROCESS OF MAKING

[75] Inventors: Robert J. Norbury, Cottage Grove; Robert W. H. Chang, Roseville; Lowell C. Zeller, Cottage Grove, all of Minn.

[73] Assignee: Minnesota Mining and Manufacturing Company, St. Paul, Minn.

[21] Appl. No.: 160,135

[22] Filed: Feb. 25, 1988

[51] Int. Cl.$^5$ .................... C11D 10/06; A61K 7/02; A61K 7/50

[52] U.S. Cl. .................... 252/174.13; 252/DIG. 5; 514/789; 514/827; 514/873; 514/919; 514/962; 514/844; 514/846; 424/59; 424/60; 424/65; 424/68; 424/DIG. 10; 428/402.2; 512/2; 512/4

[58] Field of Search .................... 428/402.2-402.22; 424/490, 496, 498, 450; 514/844, 845, 846, 847, 943, 938; 252/DIG. 5, DIG. 13, 174.13

[56] References Cited

U.S. PATENT DOCUMENTS

| | | | |
|---|---|---|---|
| 3,136,695 | 6/1964 | Tansey | 424/78 |
| 3,210,248 | 10/1965 | Feldmann | 514/873 |
| 3,516,941 | 6/1970 | Matson | 428/402.21 |
| 3,645,904 | 2/1972 | Beach | 252/DIG. 5 X |
| 3,691,270 | 9/1972 | Charle et al. | 428/402.2 X |
| 3,705,102 | 12/1972 | Mast | 252/174.13 |
| 3,798,179 | 3/1974 | Hellyer | 252/174.13 |
| 3,930,101 | 12/1975 | Vincent | 428/326 |
| 4,115,315 | 9/1978 | Marinelli | 252/DIG. 13 X |
| 4,126,674 | 11/1978 | Mausner | 252/DIG. 5 X |
| 4,450,221 | 5/1984 | Terada et al. | 430/106.6 |

FOREIGN PATENT DOCUMENTS 62-238210 10/1987 Japan.

OTHER PUBLICATIONS

Noda et al., *Patent Abstracts of Japan*, 62-161712, vol. 11, No. 398, (7/1987).

Tanaka, *Patent Abstracts of Japan*, 55-26807, vol. 4, No. 54, (2/1980).

Nakajima et al., *Patent Abstracts of Japan*, 61-254511, vol. 11, No. 106 (11/1986).

Naito et al., *Patent Abstracts of Japan*, 60-123317, vol. 11, No. 141 (12/1986).

Hasegawa, *Patent Abstracts of Japan*, 62-12707, vol. 11, No. 192 (1/1987).

*Primary Examiner*—Robert L. Stoll
*Assistant Examiner*—John M. Covert
*Attorney, Agent, or Firm*—Gary L. Griswold; Walter N. Kirn; Mark A. Litman

[57] ABSTRACT

The use of frangible microcapsules in cleansing creams and cold creams and other cosmetic products improves their cleansing, cleaning, and removal properties without damage to the skin.

23 Claims, No Drawings

ENCAPSULATED COSMETIC MATERIALS AND PROCESS OF MAKING

This application is a continuation-in-part of application Ser. No. 06/887,799, filed July 18, 1986, now U.S. Pat. No. 4,976,961.

BACKGROUND OF THE INVENTION

1. Field of the Invention

The present invention relates to skin care compositions or lotions containing liquids or oils and especially cosmetic emollient oils in microcapsules for use in the application of materials to the skin or other surfaces.

2. Background of the Art

It is fairly common to find encapsulated liquid materials in the marketplace. Technology has been available for many years to effectively provide microcapsules with liquid oleophilic ingredients. Representative processes are shown in U.S. Pat. Nos. 3,016,308 and 3,516,941. These patents disclose in situ polymerization reactions in which a hydrophobic oil phase is dispersed in an aqueous phase containing resin precursors, particularly aminoplast resin precursors (to form urea/aldehyde resins and the like). High shear agitation is used to keep the capsule size small. Addition of an acid catalyst initiates the polycondensation of the aminoplast precursors, resulting in the deposition of the aminoplast resin about the dispersed droplets of the oil phase. This produces the microcapsules.

Other polycondensation encapsulation techniques are shown in U.S. Pat. Nos. 3,429,827 and 4,000,087. These particular techniques are more limited in the classes of hydrophobic inner phases acceptable in the microcapsules because of reaction with the oil soluble monomer or poor solubility of the monomer in the desired hydrophobic phase.

U.S. Pat. No. 3,930,101 teaches that, to be retained in the hydrophobic phase during high shear dispersion of a fluid particulate dispersion, it is necessary that the particulate be preferentially wetted by the hyrophobic phase. It is suggested to use suitable surfactants which adsorb to the particulate surface as a way to achieve the desired preferential wetting. It has, however, been recognized that, in the in situ polymerization of aminoplast resins method for encapsulation, the presence of surfactants interferes with the deposition of the aminoplast resin at the hydrophobic phase/water phase interface, giving poorly formed or leaky capsules. Similarly, oil soluble suspending agents could alter the wetting of many particulates. Since many of these materials contain carboxylate groups, exposure to highly acidic medias often converts them to carboxylic acid groups altering their absorbability to the particulates.

U.S. Pat. Nos. 4,450,221 teaches magnetic toners comprising lyophilic magnetic particles and a resin surrounded by a resin wall to form microcapsules. Colorants such as pigments or dyes may be included in the wall forming resin or the toner. The magnetic particles are rendered lyophilic by treatment with a titanate or silane coupling agent. The coupling agent is said to uniformly disperse the particles in the binder resin and firmly bond the magnetic particle to the resin.

Skin cleansing soaps are known to include abrasive materials such as pumice to assist in deep cleansing or abrasive removal of detritus.

BRIEF DESCRIPTION OF THE INVENTION

Liquids, oils and especially cosmetic emollient oils generally can be encapsulated by conventional procedures such as shown in U.S. Pat. No. 3,516,941. However, even with careful control of the shear forces in the reaction vessel, the capsules tend to be too small for many commercial applications, particularly in cosmetic applications. The capsules are too difficult to rupture and are often too small to provide any mildly abrasive benefits.

It has been found that the addition of soluble or swellable polymeric materials to the oils enables them to form larger capsules without destroying the properties of the oils. In fact, the polymer also tends to aid the oil in adhering to the surface of skin and extending their benefits over a longer period of time.

It has been found that larger capsules containing cosmetic ingredients can be dispersed in skin care composition and lotion carrying media and provide additional activity including mild and controlled cleaning abrasion.

DETAILED DESCRIPTION OF THE INVENTION

In accordance with the present invention, microcapsules are prepared by polymerization such as in situ aminoplast polymerization. The techniques disclosed, generally referred to as an in situ polymerization reaction, yield, for example, an aminoplast resin capsule wall material. In the process, a liquid or oil such as a cosmetic emollient oil phase with a polymeric material dissolved therein is dispersed in an aqueous phase containing the aminoplast resin precursors by applying shear agitation. Addition of an acid catalyst initiates the polycondensation of the aminoplast precursors, resulting in the deposition of the aminoplast resin about the dispersed droplets of the oil phase, producing the microcapsules.

Typical cosmetic emollient oils are organic liquids with viscosities between 2 and 150 cp at 20° C., preferably between 2 and 100 cp. The oils preferably have molecular weights in excess of 100, more preferably in excess of 125 and most preferably between 125 and 500. Examples of commercial oils used as cosmetic emollient oils include mineral oil, castor oil, vegetable oil, corn oil, peanut oil, jojoba oil, octyl hydroxy stearate, (and other alkyl hydroxy stearates), acetylated lanolin alcohol, alkyl palmitates such as isopropyl palmitate, 2-ethylhexyl palmitate, glycerol triacetates, disopropyl adipate, dioctyl adipate (and other alkyl adipates), isopropyl myristate, $C_{12}$ to $C_{15}$ alcohol benzoates, and the like.

The polymeric additive must be dispersible or soluble in the oil so as to increase its viscosity. These materials are preferably polymers even though waxy substances may be used although with less desirable results. The polymers should be oleophilic to be wetted or soluble in the oil. Examples of preferred polymers include polyolefins, polystyrene, polybutadiene, graft or block polymers of these materials such as a polystyrene-polybutadiene-polystyrene block copolymer, polyacrylates, natural rubber (not heavily vulcanized), polyisoprene, polyisobutylene, cellulose acetate esters such as cellulose acetate butyrate and cellulose acetate proprionate, and the like. It has been found in the practice of the present invention that the increase in viscosity in the oil causes an increase in the average size of the microcapsules. This has not previously been reported.

The thickening additives most significantly increase the viscosity of the oils in order to have any effect on the size of the microcapsules. Viscosities at 20° C. must be elevated well above 50 centipoise usually above 75 centipoise and preferably above 100 centipoise to be of significant benefit in the practice of the present invention. The thickening agents should therefore be chosen to be swellable rather than completely soluble in the oil. In U.S. Pat. Nos. 3,516,941, for example, it is suggested that Piccolyte resins be added to cyclohexane solvents in the encapsulation process. Even at levels of 10% by weight or more of these resins, viscosities are well below 50 centipoise (e.g., 10% Piccoyte 19 in cyclohexane displayed a viscosity of 5 centipoise) and are insufficient at any reasonable additive level to thicken the solvent to a degree to significantly increase the microcapsule size.

The process for making the microcapsules used in the practice of the present invention utilizes the addition of viscosity increasing materials selected from the group consisting of particulates (e.g., clays and polymeric particles), waxes, and polymeric additives to liquids and oils such as cosmetic emollient oils to increase their viscosity and then using the higher viscosity oil mixtures or solutions in a microencapsulation process to produce particles of a larger size than would ordinarily be formed in encapsulation of the cosmetic emollient oil without additives under identical encapsulation reaction conditions. Polymeric additives are especially preferred because they are more consistent and repeatable in their performance and because they hold the oil better on the skin. These oils with increased viscosity are particularly beneficial in encapsulation processes where shear forces are used to maintain a dispersed phase of oil in the reaction vessel.

The shell material of the capsule may be any of the various materials known to be useful in forming capsules such as organic polymers, particularly phenolic-aldehydes, urea-aldehydes, acrylic polymers, addition polymers, and condensation polymers. The capsules are preferably between 50 and 2000 microns in diameter, more preferably between 100 and 1800 microns and most preferably between 200 and 1500 microns. Preferably they have a loading of (emollient and polymer)/(shell) at least 2:1 and preferably between 3:1 and 10:1.

Additional additives such as perfumes, pigments, antifungal agents, vitamins, sunscreens, insect repellants and even medication may be added to the oil/polymer mixture, blended with the capsules, or used independently from the oils in the skin cleansing, personal care, or lotion composition. These additives particularly when blended with the capsules after they have been made, may be dispersed in a cream, oil, powder, pancake or other media as a carrier for the capsules. In such media, the capsules would usually constitute from 2 to 50% by weight of the total cosmetic composition, preferably 3 to 40% by weight of the composition, most preferably between 4 and 20% by weight.

Skin care compositions, cleansing materials, and lotions are well known commercial products. Skin care compositions include astringents, cold creams, sunburn treatments, antifungal ointments and creams, emollient compositions, antimicrobial compositions (e.g., for treatment of acne) and the like. The skin care compositions may or may not contain any cleansing or detergent materials and usually consist of blends of various ingredients such as solvents or carrying liquids (e.g., water, oils, alcohols), thickeners, emollients, surface active agents, treatment oils (skin absorbed oils), dyes, pigments, perfumes, medicines (e.g., antifungal agents, bacteriacides, antiinflammatories, etc.) and other active agents.

Cleansing materials or compositions are typically similarly consituted as are the skin care compositions, but contain additional compounds specifically intended to assist in the cleansing of the skin. These additional materials include detergents, oil absorbing materials, and surface active agents in concentrations sufficient to cleanse the skin. Shampoos are also included in this group.

Lotions are also closely related to skin care compositions but tend to be used in a manner where they reside on the skin or treated area for generally longer periods of time.

Cleansing materials tend to be broken down themselves into different classes: cleansers, water removable cleansers, tissue-off cleansers, and detergent cleansers.

Cleansing creams and cold dreams are materials with established definitions and criteria (Harry's Cosmetology, 6th Ed., The Principles and Practice of Modern Cosmetics, Volume 1, Ralph G. Harry, 1973, Chemical Publishing Co., Inc., Chapter 5, pp. 47-63, which is incorporated herein by reference).

Cleansing and cold creams tend to fall into five general areas: (1) oil-continuous solid creams with high oil content, (2) water-continuous solid creams with high oil content, (3) water-continuous liquid creams with low oil content, (4) water-continuous liquid creams with medium oil content, and (5) oil-continuous liquid creams with medium oil content. Examples of these types of creams and their ingredients are shown below.

Oil-Continuous Solid Creams With High Oil Content

A. Wax such as beeswax, paraffin wax, wax acids, microcrystalline wax, petrolatum, esters of wax acids, borax neutralized beeswax, (e.g of $C_{20}$ to $C_{36}$ saturated acids) (15–60% by weight)
B. Oils such as mineral oil sesame oil, jojaba oil, sunflower oil, etc.
C. Emulsifiers such as sorbitol, lanolin, ceresin, carbohydrates, synthetic emulsifying agents, etc.
D. Water
E. Alcohols, e.g. isopropanol
F. Perfumes
G. Preservatives and stabilizing agents such as magnesium isostearate, magnesium sulfate, asorbic acid, etc.

Water-Continuous Solid Creams With High Oil Content

A. Waxes (as above), but in lower concentrations (2–20% by weight)
B. Water
C. Emulsifiers such as triethanolamine stearate
D. Thickeners such as hydrophilic colloids, hydrophilic celluloses, alginates, carrogheenates, or water soluble resins (polyvinyl alcohol, polyvinylpyrrolidone, etc.)
E. Perfumes
F. Preservatives Water-Continuous Solid Creams With Medium Oil Content A. Oils (containing glycerin)

B. Long chain carboxylic acids and esters (e.g., $C_{20}$–$C_{36}$ carboxylic acids such as stearic acid, palmitic acid, oleic acid, behenic acid)
C. Alkanolamines (triethanolamine)
D. Water
E. Emulsifiers (particularly anionc or nonionic emulsifiers)
F. Alcohols (e.g., cetyl alcohol)
G. Liquid waxes (e.g., liquid paraffin)
H. Perfumes
I. Preservative Water-Continuous Liquid Creams With Low Or Medium Oil Content A. Oil (1–15% by weight)
B. Long chain carboxylic acids and esters
C. Alkanolamines
D. Water
E. Emulsifiers
F. Perfume
G. Stabilizers Oil-Continuous Liquid Creams With Medium Oil Content A. More than 30% by volume oil phase
B. Alcohols (cetyl alcohol, lauryl alcohol)
C. Emolient/Emulsifier (lanolin, lanolin extracts)
D. Water
E. Perfumes
F. Stabilizers The generally larger, brittle particles of the present invention add unique benefits to the compositions and lotions in which they are used. Not only do the microcapsules release their contained liquid entirely or at least primarily at the time of being physically rubbed during application of the composition to the human body, but during this rubbing the brittle capsules provide a beneficial mild abrasive or exfoliating effect on the surface to which they are being applied. Furthermore, this abrasive action can be readily controlled by adjusting the size and/or brittleness of the capsule shells. The capsules continue to break down with continued physical action (e.g., rubbing, scrubbing, massaging) on the composition. The microcapsules can therefore be designed to provide at least a threshold minimum of abrasion and yet put a controlled upper limit on the amount of abrasion by selecting materials that will break down to a non-abrasive size with a predetermined amount of use.

The microcapsules should be able to provide measurable abrasive activity (e.g., exfoliation or reddening from abrasion) with continued physical action on compositions containing them. This abrasive activity can be checked easily against the skin on the back of ones hand. Such abrasion would not be available from gelatin capsules.

The microcapsules should be stable within the carrying medium. "Stable", means that the microcapsules will not dissolve for a period of at least one year (preferably two years) and that no more than fifty percent the microcapsules should float to the top or settle to the bottom of the compositions in less than six months, preferably less than twenty-five percent of the microcapsules will settle or float in one year.

All viscosities in the Examples were measured at ambient (room) temperature unless otherwise stated.

EXAMPLE 1

To 900 grams of a mixture of $C_{12}$–$C_{15}$ alcohol benzoates was added 100 grams of a styrene-isoprene-styrene block copolymer (Kraton ® D1107). The mixture was heated for four hours at 120° C. until the copolymer had dissolved. The thickened oil was encapsulated in a urea-formaldehyde capsule according to the teachings of U.S. Pat. No. 3,516,941 with the shear rate controlled to generate capsules having an average diameter between 300 and 400 microns. These capsules could be rubbed onto the skin, either directly by hand or with a brush applicator and ruptured. The oils would spread evenly on the skin and the broken capsule shells provide a useful, mildly abrasive action on the skin.

EXAMPLE 2

720 grams of a mixture of $C_{12}$–$C_{15}$ alcohol benzoates were mixed with 80 grams of the block copolymer of Example 1 and heated to 120° C. with stirring until completely dissolved. The solution was cooled to 60° C. and 200 grams of a commercially available bactericide (Irgasons-300) was added to 790 grams of the solution. This mixture was cooled to 40° C. and 10 grams of fragrance was added with stirring. This solution was then encapsulated according to the procedures of Example 1. The capsules were useful as a directly applied underarm deodorant composition. The capsules could also be blended with a wax or cream to form a composition then could be applied to the underarms. The natural movement of the arms is sufficient to rupture the capsules over a period of time.

EXAMPLES 3–5

Twenty-five grams of the copolymer of Example 1 were dissolved in 975 grams of octyl hydroxystearate. The mixture was heated to 100° C. with stirring and dissolved in the manner described below.

The details of the encapsulation process are as follows:

(3) To a one-liter baffled reactor were charged 379 gm urea-formaldehyde precondensate and 181 gm water. Vigorous mixing was applied and 80.1 gm sodium chloride and 0.53 gm sodium carboxymethyl cellulose were added. To the reactor was then added 250.8 gm of the fill material of Example 1 and precise temperature and mixing speed were applied. Sulfuric acid catalyst was added to achieve a pH of 2.3. This condition was held for two hours followed by an increase in temperature to 140° F. for 2 hours. The reaction was cooled to room temperature and neutralized to a pH of 8.0. The resulting capsules were filtered, washed, and dried. The excellent quality capsules were determined to have a median size of 354 microns.

(4) To a one liter baffled reactor were charged 303.2 gm urea-formaldehyde precondensate and 221 gm water. Vigorous mixing was applied, followed by the addition to the reactor of 37.8 gm sodium sulfate and 0.5 gm sodium carboxy- methyl cellulose. After achieving solution 297 gm of the fill material, as of Example 2, was added. Precise mixing speed and temperature control were applied followed by the addition of sulfuric acid to pH 2.3. Conditions were held for three hours followed by temperature increase to 140° F for two hours. The excellent quality capsules having a median size of 61 microns were filtered, washed, and dried to a slightly clumped product.

(5) To a 19 liter baffled reactor were added 7525 gm urea-formaldehyde precondensate and 4000 gm water. Vigorous mixing was applied followed by addition of 1650 gm sodium chloride and 11.0 gm sodium-carboxymethyl cellulose. After obtaining solution 4465 gm of the fill of Example 3 was added. Precise temperature and turbine speed controls were established, followed by addition of dilute hydrochloric acid to a pH of 2.31. This condition was held for two hours followed by a temperature increase to 140° F. for 1.75 hours. The resulting capsules having a median size of 330 microns were of excellent quality.

EXAMPLES 6 AND 7

To 180 ml refined jojoba bean oil having a viscosity of 33 centipoise was added 70 ml Amoco Indopol H-100 polybutene. The resulting mixture had a measured viscosity of 106 centipoise and was encapsulated.

226.1 gm Carnation Mineral Oil and 2.3 gm Kraton 1107 were charged to a wide-mouth jar and were alternately heated on a steam bath and shaken until solution was achieved. The viscosity of the mineral oil increased from its initial value of 19 centipoise to 460 centipoise with the Kraton. This was encapsulated.

The encapsulation process for these oils was the same as described above.

EXAMPLES 8-12

These examples show the effectiveness of viscosity increasing additives in generating larger capsule shells under otherwise identical reaction conditions.

EXAMPLE 8

To a one liter baffled reactor were charged 379 gm urea-formaldehyde precondensate and 181 gm water. Vigorous mixing was applied and 80.1 gm sodium chloride and 0.53 gm sodium carboxymethyl cellulose were added. To the reactor was then added 250.8 gm of the fill material described in Example 1 and precise temperature and mixing speed were applied. Sulfuric acid catalyst was added to achieve a pH of 2.3. This condition was held for two hours followed by an increase in temperature to 140° F. for two hours. The reaction was cooled to room temperature and neutralized to a pH of 8.0. The resulting capsules were filtered, washed, and dried. The excellent quality capsules were determined to have a median size of 354 microns. A similarly-run encapsulation reaction using the unmodified fill material yielded a median capsule size of 155 microns.

EXAMPLE 9

To a one liter baffled reactor were charged 303.2 gm urea-formaldehyde precondensate and 221 gm water. Vigorous mixing was applied followed by addition to the reactor of 37.8 gm sodium sulfate and 0.5 gm sodium carboxymethyl cellulose. After achieving solution, 297 gm of the fill material as described in Example 2 was added. Precise mixing speed and temperature control were applied followed by addition of sulfuric acid to pH 2.3. Conditions were held for three hours followed by temperature increase to 140° F for two hours. The excellent quality capsules having a median size of 61 microns were filtered, washed, and dried to a slightly clumped product. Capsules similarly prepared using unmodified fill had a median size of 32 microns.

EXAMPLE 10

To a 19 liter baffled reactor were added 7525 gm urea-formaldehyde precondensate and 4000 gm water. Vigorous mixing was applied followed by addition of 1650 gm sodium chloride and 11.0 gm sodium carboxymethyl cellulose. After obtaining solution 4465 gm of the fill as described in Example 3 were added. Precise temperature and turbine speed controls were established followed by addition of dilute hydrochloric acid to a pH of 2.31. This condition was held for two hours followed by a temperature increase to 140° F. for 1.75 hours. The resulting capsules having a median size of 330 microns were of excellent quality. Capsules of unmodified fill from a similar encapsulation reaction had a median size of 145 microns.

EXAMPLE 11

To a one liter baffled reactor were charged 376 gm urea-formaldehyde precondensate and 200 gm water. Vigorous mixing was applied followed by addition to the reactor of 82.5 gm sodium chloride and 0.55 gm sodium carboxymethyl cellulose. After obtaining solution, 216 gm of the mixture as described in Example 4 was added. Precise mixing speed and temperature controls were applied followed by addition of hydrochloric acid to pH of 2.3. This condition was held for two hours followed by an increase in temperature to 140° F. for 1.9 hours. The resulting capsules were of excellent quality and had a median size of 186 microns. Unmodified fill when encapsulated via a similar method yielded capsules having a median size of 146 microns.

EXAMPLE 12

An encapsulation was performed using the procedure as summarized in Example 11 but substituting 250 ml of fill as described in Example 7. The resulting capsules were of excellent quality having a median size of 249 microns. The unmodified fill yielded capsules of 170 microns median size.

Using the procedure in Example 11 using 250 ml of the mineral oil/Kraton as described in Example 7 as the fill material. The resulting capsules were of varying quality and had an average size of 315 microns.

EXAMPLES 13-15

(13) 352 gm of N,N-diethyl toluamide (DEET) was mixed with heating with 48 gm Kratons 1107 until dissolved. The viscosity of the resulting solution measured 91 centipoise; unthickened DEET measured 17.5 centipoise.

(14) 225 gm of a commercially purchased oil base wood stain having a measured viscosity of 4 centipoise was mixed and heated with 25 gm Kraton® D1107 until solution was achieved. This mixture had a viscosity of 74 centipoise.

(15) 368 gm of Escalol 507 (2-ethyl hexyl para-dimethylaminobenzoate) was stirred with 32 gm Kraton® D1107 while being heated on a steam bath until a solution was achieved. The resulting solution has a measured viscosity of 1240 centipoise compared with a viscosity of 60 centipoise for the unmodified Escalol.

EXAMPLE 16

As in the procedure used in Example 11, using the fill material 13) shown above, capsules with an average diameter of 101 microns were produced. The unmodified DEET provided capsules of 81 microns under otherwise identical conditions.

EXAMPLE 17

Using the procedures of Example 11 with the fill material (14) described above, capsules with an average diameter of 265 microns were produced. The unmodified wood stain provided capsules with average diameter of 127 microns under otherwise identical conditions.

EXAMPLE 18

Using the procedure of Example 11 with 250 ml of the Escalol/Kraton as described in (15) above as the fill material, microcapsules were formed. The resulting capsules were of varying quality and had a median volume size of 326 microns; unmodified fill encapsulated in similar fashion yielded capsules of 165 micron size.

The abrasiveness of materials with respect to skin exfoliation can be quantified by measuring the amount of fluorescence lost from skin which has been stained with a particular amount and type of fluorescent dye (in these examples, dansyl chloride was used). Fluorescence is measured before and after exfoliation with the abrasive.

Capsules of Example 10 were used at 5, 8, and 10% by weight levels in a detergent cream cleanser base. Exfoliation properties were determined in comparison to (A) a cleansing cream soap, (B) 5% capsules in a cream, (C) 8% capsules in a cream, and (D) 10% capsules in a gel cleanser and (E) a commercial cleansing cream with crushed apricot pits.

A block of at least four test sites, approximately 3 cm in diameter, was mapped out on the middle back of all subjects. A previously prepared 0.1 ml aliquot of a 5% suspension of dansyl chloride in a white petrolatum base was then applied to each test site using an occlusive dressing. After a twenty-four (24) hour exposure, the patches were removed and the areas gently washed and blotted dry with a soft terry cloth towel to remove unincorporated dye. The sites were then allowed an additional twenty-four (24) hour air exposed resting period before application of test products.

On day three of the study, the subjects returned to the test laboratory to have the test sites photographed under carefully controlled conditions including UV illumination. Approximately 0.25 gm of each test product was applied to the test sites according to a predetermined randomization schedule.

Control and treatment sites were cleansed for thirty (30) seconds using a rapid circular motion, medium hand pressure and tepid water. Fingers were used to cleanse both the treatment and control sites. Lather from a cream cleansing bar were used on the control sites, and the compositions were then used to cleanse the treatment sites. After cleansing, test sites were rinsed with tepid water, patted dry, and again photographed under UV light. This procedure of treatment, then photographing the treated sites was repeated an additional three times, or until all test products could be visually differentiated from the control site.

To assure uniformity of photographs, all film used in this study was from the same bulk roll of film, and was submitted for special batch processing. Uniformity of photographs is important as they were examined by a Nikon Magiscan 2A Image Analysis system for a quantitative determination of the percent decrease in florescence as compared to control. The greater the decrease in florescence, the greater the exfoliating capacity of the treatment.

The commercial cream cleansing bar (A) provided essentially 0% reduction in fluorescence as compared to a water wash. The apricot abrasive (E) produced a 12.4% further reduction in fluoresence, and the compositions (B, C, D) of claims 16, 17, and 18 provided a reduction in fluorescence of 2.5%, 4% and 6%.

It is thus preferred to have an amount of brittle microcapsules present in the material to be applied to the skin which can reduce fluorescence by at least 1%, preferably at least 2%, and most preferably at least 2.5%, but not greater than 10% (to prevent overscrubbing) than is reduced by tepid water washing under equivalent applied pressure to the skin area.

EXAMPLES 19 AND 20

The following compositions are examples of a cleansing cream formulation and cleansing gel formulation that are best modes of producing the invention.

| 19. Ingredients | % W/W |
|---|---|
| PART I | |
| A. Deionized Water | 48.02 |
| B. Magnesium Aluminum Silicate | 1.7 |
| C. Lauroamphocarboxyglycinate (30% Active) | 2.9 |
| D. Sodium Lauroyl Sarcosinate (30% Active) | 9.5 |
| E. Cocamidopropyl Hydroxysultaine (43% Active) | 4.8 |
| F. Mixture of Special Fatty Alcohol Ether Sulfates (30% Active) | 4.8 |
| G. Sodium Laureth Sulfate (26% Active) | 5.5 |
| H. Lactic Acid (88% Active) | 0.43 |
| PART II | |
| I. Glyceryl Stearate (and) PEG-100 Stearate | 4.8 |
| J. Lauric/Linoleic Diethanolamide | 1.4 |
| K. Laureth - 4 | 1.2 |
| L. Cetearyl Alcohol (and) Polysorbate 60 | 0.90 |
| M. PPG-15 Stearyl Ether | 1.2 |
| N. Shea Butter | 0.90 |
| O. Sodium Cocoyl Isethionate (80% Active) | 5.7 |
| P. Latex Opacifier [Sodium Styrene/Acrylates/ Divinylbenzene Copolymer (and) Ammonium Nonoxynol - 4 Sulfate] | 0.90 |
| Q. Preservative [Propylene Glycol (and) Diazolidinyl Urea (and) Methylparaben (and) Propylparaben | 0.25 |
| R. Fragrance Oil | 0.10 |
| S. 3M Microcapsules (3.9% Octyl Hydroxystearate 1.0% U/F Resin, 0.1% Styrene Isoprene Copolymer | 5.0 |

Process: First, Part I is prepared by dispersing B in A while mixing heating to 82° C., and sequentially adding through H to this part. Meanwhile, Part II is prepared by combining ingredients I through N is separate vessel, mixing, and heating to 74°. Then, ingredient O is dispersed in this part. Next, with continued mixing, Part II is slowly added to Part I. Then ingredient P is added to mixing batch while at 74° C., batch is cooled to 47° C., and ingredients Q, R, and S are sequentially added to mixing batch. Batch is completed after mixing to ensure uniformity.

| 20. Ingredients | % W/W |
|---|---|
| A. Deionized Water | 58.97 |
| B. FD&C Blue No. 1 | 0.0004 |
| C. Carbomer 1342 | 0.94 |
| D. Lauroamphocarboxyglycinate (30% Active) | 11.4 |
| E. Ammonium Lauryl Sulfosuccinate (40% Active) | 11.0 |
| F. Cocamidopropyl Hydroxysultaine (43% Active) | 9.2 |
| G. Cocamide DEA | 1.4 |

-continued

| 20. Ingredients | % W/W |
|---|---|
| H. PEG-30 Glyceryl Cocoate | 0.63 |
| I. Ammonium Hydroxide Concentrated | 0.105 |
| J. Preservative [Propylene Glycol (and) Diazolidinyl Urea (and) Methylparaben (and) Propylparaben] | 0.25 |
| K. Fragrance Oil | 0.10 |
| L. Microcapsules, 3M (4.68% Octyl Hydroxy Stearate, 1.2% U/F Resin, 0.12% Styrene Isoprene Copolymer | 6.0 |

Process: First, ingredient B is dissolved in mixing ingredient A. Then ingredient C is slowly added and batch is mixed at room temperature until C is completely and uniformly dispersed. Then batch is heated to 82° C., and ingredients D, E, F, G, H, and I are added sequentially to mixing batch (care is taken to avoid foaming and air entrapment). Next batch is cooled to 47° C. and ingredients J, K, and L are added sequentially. Batch is completed after mixing to ensure uniformity.

This is an example of a skin cleansing composition which contains special mild synthetic detergents, nonionic surfactants/emulsifiers, thickeners, and other ingredients. Some examples of these ingredients are given below.

Synthetic detergents (a)

Amphoteric
Lauroamphocarboxyglycinate
Cocoamphocarboxyglycinate
Cocoamphocarboxypropionate
Cocamidopropyl hydroxysultaine
Cocamidopropyl Betaine
Coco-betaine (b)

Anionic
Sodium Lauroyl Sarcosinate
Sodium Laureth Sulfate
Mixture of special fatty alcohol ether sulfates
Sodium Trideceth Sulfate
Sodium Trideceth-7-carboxylate
Sodium Laureth-13-carboxylate
Sodium Cocoyl Isethionate
Sodium Methyl Cocoyl Taurate
Ammonium Lauryl Sulfosuccinate
Sodium Laureth Sulfosuccinate
Sodium Lauriminodipropionate Nonionic surfactants/emulsifiers Glyceryl Stearate (and) PEG-100 Strearate
Cetearyl Alcohol (and) Polysorbate 60
PEG-30 Glyceryl Cocoate
PEG-82 Glyceryl Tallowate
Ceteareth-20
Steareth-100
PEG-10 Soya Sterol
Poloxamer 188
Cocamide DEA
Lauric/Linoleic Diethanolamide Thickeners Magnesium Aluminum Silicate
Montmorillonite
Carbomer 934, 940 or 1342
Hydroxyethylcellulose
Hydroxypropyl Methylcellulose
Xanthan Gum
Guar Gum
Hydroxypropyl Guar Other ingredients Emollients
Buffering agents
Opacifiers
Preservatives
Fragrances

We claim:

1. Stable compositions which can be applied to the skin comprising liquid cleansers of cosmetic creams comprising brittle microcapsules with encapsulated oil therein useful in applications to skin said microcapsules comprising an oil having at least one polymetric thickener therein encapsulated by a polymeric shell consisting essentially of addition polymers, condensation polymers, phenolic aldehydes, urea aldehydes or acrylic polymer, said oil without polymeric thickeners having a viscosity at 20° C. of between 2 and 150 cp, said microcapsules having average diameters between 50 and 2500 microns, wherein said cleaner comprises at least a synthetic detergent, surfactant, and thickener, and wherein said cosmetic creams are compositions selected from the group consisting essentially of a. creams comprising wax, oil, and emulsifier,
   b. creams comprising wax, water, emulsifier, and thickener,
   c. creams comprising oils containing glycerin, long chain carboxylic acids and esters, alkanolamines, and emulsifiers,
   d. creams comprising oil, long chain carboxylic acids and esters, alkanolamines, emulsifiers, and stabilizers, and
   e. creams comprising more than 30% by volume oil, alcohols, emollient, and water.

2. The compositions of claim 1 wherein said microcapsules have average diameters between 100 and 2000 microns.

3. The compositions of claim 1 wherein said microcapsules have average diameters between 200 and 1500 microns.

4. The compositions 1 of claim 1 wherein said oil is an emollient oil and the oil plus thickener has a viscosity between 300 and 1500 cp at 20° C.

5. The compositions of claim 2 wherein said oil is an emollient oil and the oil plus thickener has a viscosity between 300 and 1500 cp at 20° C.

6. The compositions of claim 3 wherein said oil is an emollient oil and the oil plus thickener has a viscosity between 300 and 1500 cp at 20° C.

7. The compositions of claim 1 wherein said oil is an emollient oil and is selected from the group consisting of mineral oil, castor oil, jojoba oil, vegetable oil, octyl hydroxystearate, $C_{12}$–$C_{15}$ alcohol benzoates, isopropyl palmitate and isopropyl myristate.

8. The compositions of claim 2 wherein said oil is an emollient oil and is selected from the group consisting of mineral oil, castor oil, jojoba oil, vegetable oil, octyl hydroxystearate, $C_{12}$–$C_{15}$ alcohol benzoates, isopropyl palmitate and isopropyl myristate.

9. The compositions of claim 3 wherein said oil is an emollient oil and is selected from the group consisting of mineral oil, castor oil, jojoba oil, vegetable oil, octyl hydroxystearate, $C_{12}$–$C_{15}$ alcohol benzoates, isopropyl palmitate and isopropyl myristate.

10. The compositions of claim 1 wherein said polymeric thickening agent is selected from the group consisting of polyolefins, polybutadiene, polystyrene, polyacrylics, gelatin, natural rubber, polyisoprene, cellulose acetate esters and copolymers thereof.

11. The compositions of claim 2 wherein said polymeric thickening agent is selected from the group consisting of polyolefins, polybutadiene, polystyrene, polyacrylics, gelatin, natural rubber, polyisoprene, cellulose acetate esters and copolymers thereof.

12. The compositions of clam 3 wherein said polymeric thickening agent is selected from the group consisting of polyolefins, polybutadiene, polystyrene, polyacrylics, gelatin, natural rubber, polyisoprene, cellulose acetate esters and copolymers thereof.

13. The compositions of claim 5 wherein said polymeric thickening agent is selected from the group consisting of polyolefins, polybutadiene, polystyrene, polyacrylics, gelatin, natural rubber, polyisoprene, cellulose acetate esters and copolymers thereof.

14. The compositions of claim 8 wherein said polymeric thickening agent is selected from the group consisting of polyolefins, polybutadiene, polystyrene, polyacrylics, gelatin, natural rubber, polyisoprene, cellulose acetate esters and copolymers thereof.

15. The compositions of claim 9 wherein said polymeric thickening agent is selected from the group consisting of polyolefins, polybutadiene, polystyrene, polyacrylics, gelatin, natural rubber, polyisoprene, cellulose acetate esters and copolymers thereof.

16. The composition of claim 4 further comprising as a carrying medium for said microcapsules at least three ingredients selected from the group consisting of oils, alcohols, surface active agents, detergents, dyes, and thickening agents.

17. The composition of claim 10 further comprising as a carrying medium for said microcapsules at least three ingredients selected from the group consisting of oils, alcohols, surface active agents, detergents, dyes, and thickening agents.

18. Stable compositions which can be applied to the skin comprising a cosmetic cream comprising brittle microcapsules of encapsulated oil useful in applications to skin comprising an oil having at least one polymeric thickener therein encapsulated by a polymeric shell consisting essentially of addition polymers, condensation polymers, phenolic aldehydes, urea aldehydes, or acrylic polymer, said microcapsules having average diameters of between 200 and 1500 microns, said oil is an emollient oil and the oil plus thickener has a viscosity between 30 and 1500 cp at 20° C., wherein said cosmetic cream is selected from the group consisting essentially of a. oil-continuous solid creams with high oil content,
b. water-continuous solid creams with high oil content,
c. water-continuous solid creams with medium oil content,
d. water-continuous liquid creams with low or medium oil content, and
e. oil-continuous liquid creams with medium oil content.

19. The stable composition of claim 18 in which said cream is an oil continuous solid cream with high oil content.

20. The stable composition of claim 18 in which said cream is a water-continuous solid cream with high oil content.

21. The stable composition of claim 18 in which said cream is a water-continuous solid cream with medium oil content.

22. The stable composition of claim 18 in which said cream is a water-continuous liquid cream with low or medium oil content.

23. The stable composition of claim 18 in which said cream is an oil-continuous liquid cream with medium oil content.

* * * * *

UNITED STATES PATENT AND TRADEMARK OFFICE
CERTIFICATE OF CORRECTION

PATENT NO. : 5,013,473
DATED : May 7, 1991
INVENTOR(S) : Robert J. Norbury, Robert W.H. Chang and Lowell C. Zeller It is certified that error appears in the above-identified patent and that said Letters Patent is hereby corrected as shown below:

Column 3, line 15, "Piccoyte" should read --Piccolyte--.
Column 4, line 23, "cold dreams" should read
--cold creams--.
Column 4, line 43, "mineral oil" should be followed
by a comma.
Column 12, line 18, "polymetric" should read --polymeric--.
Column 12, line 47, "1 of claim 1" should read
--of claim 1--.

Signed and Sealed this

Twenty-sixth Day of October, 1993

Attest:

BRUCE LEHMAN

Attesting Officer

Commissioner of Patents and Trademarks